United States Patent [19]
Dekel et al.

[11] Patent Number: 5,810,008
[45] Date of Patent: Sep. 22, 1998

[54] APPARATUS AND METHOD FOR VISUALIZING ULTRASONIC IMAGES

[75] Inventors: Doron Dekel, North York; Charles Ryan Hall, Toronto, both of Canada

[73] Assignee: ISG Technologies Inc., Mississauga, Canada

[21] Appl. No.: 758,721

[22] Filed: Dec. 3, 1996

[51] Int. Cl.$^6$ ........................................................ A61B 8/00
[52] U.S. Cl. ........................................ 128/660.07; 128/916
[58] Field of Search ......................... 128/660.01, 660.07, 128/662.05, 916, 662.06

[56] References Cited

U.S. PATENT DOCUMENTS

| | | |
|---|---|---|
| 4,058,114 | 11/1977 | Soldner . |
| 4,407,294 | 10/1983 | Vilkomerson . |
| 4,501,278 | 2/1985 | Yamaguchi et al. . |
| 4,899,756 | 2/1990 | Sonek . |
| 5,158,088 | 10/1992 | Nelson et al. ................... 128/662.05 |
| 5,161,536 | 11/1992 | Vilkomerson et al. ............ 128/660.07 |
| 5,251,127 | 10/1993 | Raab . |
| 5,261,404 | 11/1993 | Mick et al. . |
| 5,311,871 | 5/1994 | Yock . |
| 5,398,690 | 3/1995 | Batten et al. . |
| 5,443,489 | 8/1995 | Ben-Haim . |
| 5,515,853 | 5/1996 | Smith et al. . |
| 5,608,849 | 3/1997 | King, Jr. ............................. 395/119 |

OTHER PUBLICATIONS

Shi Sherebrin et al., Freehand Three–Dimensional Ultrasound: Implementation and Applications, Robarts Research Institute, Department of Radiology, University Hospital, Department of Medical Biophysics, University of Western Ontario, London, Canada.

*Primary Examiner*—Francis Jaworski
*Attorney, Agent, or Firm*—Orange & Associates

[57] ABSTRACT

The present invention provides a system and method for visualizing internal images of an anatomical body. Internal images of the body are acquired by an ultrasound imaging transducer. The position and orientation of the ultrasound imaging transducer is tracked in a frame of reference by a spatial determinator. The position of the images in the frame of reference is determined by calibrating the ultrasound imaging transducer to produce a vector position of the images with respect to a fixed point on the transducer. This vector position can then be added to the position and orientation of the fixed point of the transducer in the frame of reference determined by the spatial determinator. The position and orientation of a medical instrument used on the patient are also tracked in the frame of reference by spatial determinators. The position and orientation of the instrument is mapped onto the position and orientation of the images. This information is used to generate processed images from the images acquired by the transducer. The processed images are generated from a view spatially related to the position of the instrument. The system is expandable so that more than one instrument and more than one transducer can be used.

11 Claims, 6 Drawing Sheets

# APPARATUS AND METHOD FOR VISUALIZING ULTRASONIC IMAGES

FIELD OF THE INVENTION

The invention relates generally to the field of ultrasound imaging. In particular, the present invention relates to processing ultrasound images from an ultrasound transducer. More specifically, the invention relates to a method and system for determining the spatial position of a medical instrument and of the images being acquired by the ultrasound imaging transducer and using this information to generate processed images of the body from the view or perspective of the instrument.

BACKGROUND OF THE INVENTION

It is known in the art to use ultrasound imaging systems to acquire internal images of a body, such as an anatomical body, in order to plan or perform a medical procedure, be it diagnostic, therapeutic or surgical. There are several advantages to using ultrasound imaging systems over other imaging systems. For example, ultrasound imaging systems tend to be less intrusive on the body and do not expose the patient to large amounts of radiation or dyes. In addition, ultrasound imaging systems tend to be less expensive to purchase. Ultrasound imaging systems also tend to be less expensive to operate because there are fewer personnel involved, it is not necessary to keep the patient stable, and the ultrasound images need not be "pre-acquired", but can be acquired during the medical procedure.

The principal advantage of imaging systems in general is the ability to visualize internal regions of a patient and to guide medical instruments or probes within the body of a patient without making large incisions into the body of the patient. Making smaller incisions into the body of the patient decreases the risk for the patient and also the duration of the patient's hospital stay.

However, to effectively use images as a navigational aid during a procedure on the patient, the images being acquired by the ultrasound imaging transducer must be displayed in a clear, accurate and user-friendly manner. Only then can the medical practitioner easily visualize the internal region of the body.

In the past, the images acquired by an ultrasound imaging transducer could only be viewed from one perspective or view, namely from the perspective of the ultrasound imaging transducer which was acquiring the images. While the imaging transducer could be moved around the body to acquire images from different perspectives or views, it was not possible to acquire images from the perspective or view of the instrument. The medical practitioner would be left with the task of extrapolating the position, orientation and course of the instrument in the body from the images on the display.

In addition, the position of the instrument in prior art systems is generally not easily seen on the acquired images. To improve visibility of the instrument, it was often necessary to place an ultrasound tracking transducer on the instrument. The ultrasound tracking transducer would receive the ultrasound signals emitted by the ultrasound imaging transducer and provide a "blip" to represent the instrument on the images. But this would require modified instruments and additional cost.

Therefore, the prior art has suffered from several disadvantages. In particular, the prior art systems could only generate and display clear ultrasound images from one perspective or view, namely from the perspective or view of the ultrasound imaging transducer. However, this view provides a poor navigational tool for a medical practitioner at least because the medical practitioner cannot easily visualize the course of the instrument in the body.

In addition, most of the prior art systems require that a tracking transducer of some type be located on the probe or medical instrument which was inserted into the body of the patient. Modified instruments incorporating tracking transducers must be used.

Accordingly, there has been a need in the art for an alternative method and system for accurately, efficiently and robustly presenting the images acquired from an ultrasound imaging transducer. In addition, there is a need for a system which does not require the medical instruments to have ultrasound tracking transducers which enter the body.

SUMMARY OF THE INVENTION

Accordingly, it is an object of this invention to at least partially overcome the disadvantages of the prior art. Also, it is an object of this invention to provide an improved method and system for easily presenting enhanced images from the ultrasound imaging transducers, including three dimensional images of the internal regions of the patient, from the perspective or view of the instrument in the body, such that the view is related to the position and orientation of the instrument with respect to the patient. It is also an object of the present invention to provide a method and apparatus for tracking the spatial position of the medical instrument and the ultrasound imaging transducer and using this information to automatically generate images from the perspective or view of the instrument, with or without a representation of the instrument on the images.

Accordingly, in one of its aspects, this invention relates to a method for visualizing internal images of a body in relation to an instrument within the body, said images having been acquired by an ultrasound imaging transducer, said method comprising the steps of: (a) obtaining spatial positional information of the instrument comprising a position and an orientation of the instrument in a frame of reference; (b) obtaining spatial positional information of each of the images of the body acquired by the ultrasound imaging transducer comprising a position and an orientation of the images in the frame of reference; (c) determining the position and orientation of the instrument relative to the position and orientation of the images; (d) processing the images to generate processed images from a view which is spatially related to the position of the instrument; and (e) displaying the processed images of the body on a display.

In a further aspect, the present invention provides a method for obtaining the spatial positional information of the images in the frame of reference comprises the steps of: (a) determining spatial positional information of the images with respect to the transducer; (b) obtaining spatial positional information of the transducer comprising a position and an orientation of the transducer in the frame of reference; and (c) determining the position of the acquired images in the frame of reference from the spatial positional information of the transducer in the frame of reference and the spatial positional information of the images with respect to the transducer.

In a still further aspect, this invention relates to a system for visualizing internal images of a body in relation to an instrument within the body, said images having been acquired by an ultrasound imaging transducer, the system comprising: first spatial determinator means for determining spatial positional information of the instrument comprising a position and an orientation of the instrument in a frame of reference and for sending a first spatial signal representing the spatial positional information of the instrument; second spatial determinator means for determining spatial positional information of the ultrasound imaging transducer comprising a position and an orientation of the ultrasound imaging transducer in the frame of reference and for sending a second spatial signal representing the spatial positional information of the transducer; mapping means for receiving the first spatial signal and the second spatial signal and generating a first mapping signal indicative of the position and orientation of the instrument relative to the position and orientation of the images; image processing means for receiving the first mapping signal and signals representing the images acquired by the transducer and generating processed images from a view which is spatially related to the position of the instrument; and display means for displaying the processed images.

Further aspects of the invention will become apparent upon reading the following detailed description and the drawings which illustrate the invention and preferred embodiments of the invention.

BRIEF DESCRIPTION OF THE DRAWINGS

In the drawings, which illustrate embodiments of the invention.

DETAILED DESCRIPTION OF PREFERRED EMBODIMENTS OF THE INVENTION

Figure 1:
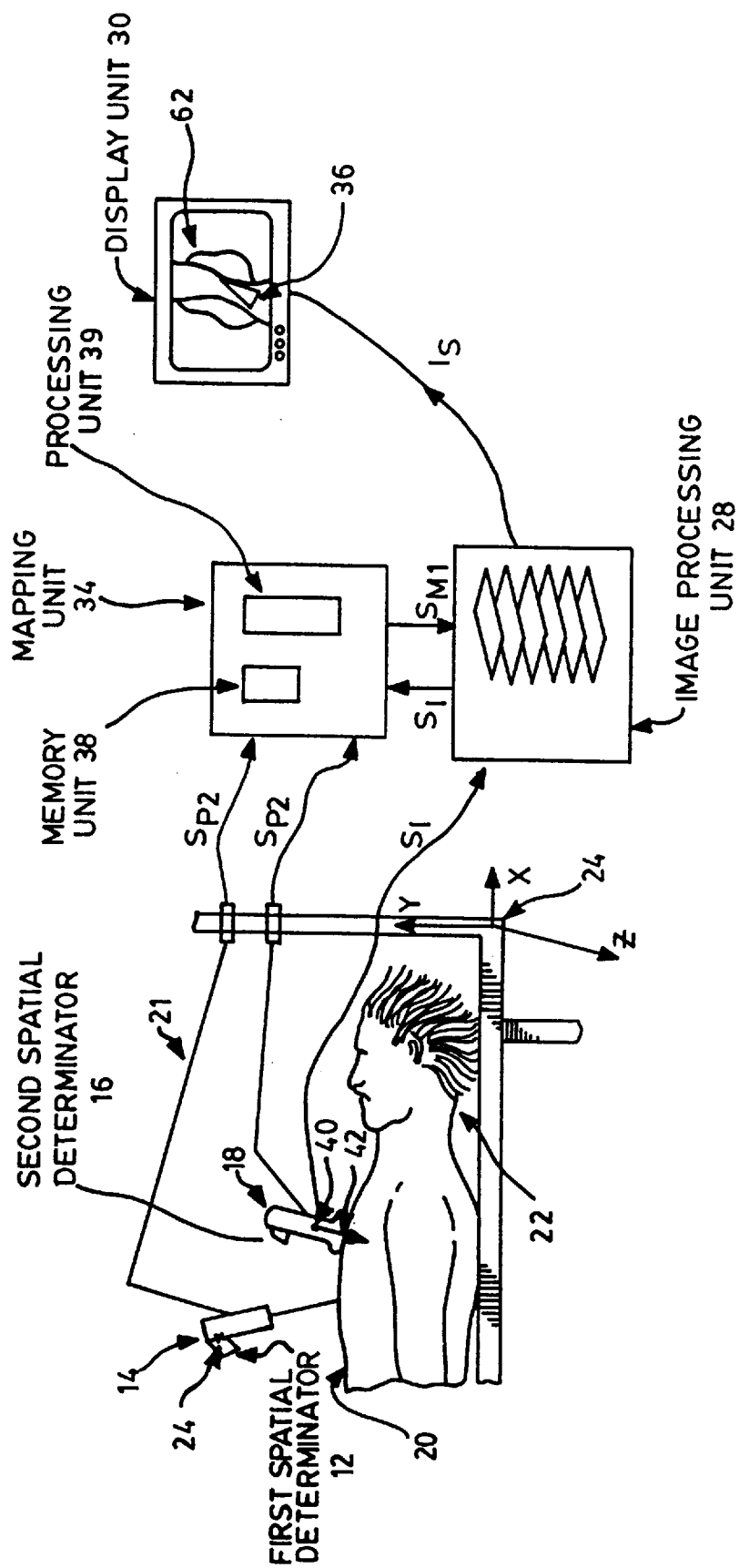
FIG. 1 shows a system according to one embodiment of the present invention.

The visualizing system of the present invention is shown generally in FIG. 1 by reference numeral 10. The system 10 comprises a first spatial determinator, shown generally as 12, for determining spatial positional information of a surgical instrument 14. The spatial positional information determined or obtained by the first spatial determinator 12 comprises the position and the orientation of the instrument 14 in a frame of reference. The first spatial determinator 12 also sends a first spatial signal $SP_1$ representing the spatial positional information of the instrument 14 in the frame of reference.

In a similar manner, the system 10 comprises a second spatial determinator 16 for determining spatial positional information of an ultrasound imaging transducer 18. The spatial positional information of the transducer 18 comprises the position and the orientation of the transducer 18 in the frame of reference. The second spatial determinator 16 sends a second spatial signal $Sp_2$ representing the spatial positional information of the transducer 18 in the frame of reference.

The spatial positional information of an object comprises at least sufficient information to identify the spatial position, namely the position and orientation, of an object in a frame of reference. In a Cartesian coordinate system, the position of an object can be indicated by the x, y and z co-ordinates, which uniquely identify the position in three dimensions. The orientation of an object can be represented by azimuth (a), elevation (e) and roll (r). Accordingly, the first spatial signal $Sp_1$ identifies the spatial position of the instrument 14 by representing the spatial positional information of the instrument 14, such as the x y z co-ordinates and the azimuth, roll and elevation.

The first and second spatial determinators 12, 16 can determine the position and orientation of the instrument 14 and the ultrasound imaging transducer 18, respectively, relative to a frame of reference. There are a number of alternate methods and apparatuses which can be used to obtain the spatial positional information of the instrument 14 and the ultrasound imaging transducer 18 relative to the frame of reference. Apparatuses which can perform this function are known in the art and will be collectively referred to as spatial determinators, such as the first and second spatial determinators 12, 16.

For example, a spatial determinator which may be used in the system 10 as either the first spatial determinator 12, the second spatial determinator 16, or both, comprises an electromagnetic emitter positioned at a fixed point (shown by reference numeral 24' in FIG. 1) in a frame of reference and a sensor located on the instrument 14 and a corresponding sensor located on the transducer 18. By comparing the timing and phase of transmitted signals from the emitter to received signals picked up by the sensors, the position and the orientation of the instrument 14 and the transducer 18 relative to the fixed point 24' can be determined. As a further example of spatial determinators, the instrument 14 could be attached to a multi-joint light-weight arm 21 having several sections joined together by joints. The joints in combination provide for a range of motion equal to or greater than that required for a given procedure. Angular sensors detect any change in the position or orientation of the sections and joints. Using simple geometric calculations and this angular information, the position and orientation of the instrument 14 relative to the fixed point 24' can be determined. A similar spatial determinator could be used for the transducer 18. Spatial determinators using these known locating methods are commercially available.

It should be noted that any sensors located on or near the instrument 14 in the system 10 need not be located in a position on the instrument 14 which enters the body 20 of the patient 22. For example, the sensor could be located at any location on the instrument 14, or on the arm 21 used to hold the instrument 14. In this way, the sensor of the first spatial determinator 12 is always accessible to the persons using the system 10 so that it can be checked and replaced if found to be faulty. Also, the sensor of the first spatial determinator 12 need not be a particular size and shape so as to permit entry into the body 20 of the patient 22.

It is preferable that the fixed point 24' from which the spatial determinators 12, 16 determine spatial positional information of the instrument 14 and the transducer 18 is also the origin (shown in FIG. 1 by reference numeral 24) for the frame of reference. Three axes are shown radiating from the origin 24 representing the x, y and z coordinates in the frame of reference. Each point in the frame of reference, and in particular each point in and around the patient 22, has a unique x, y and z coordinate in this frame of reference. The spatial determinators 12, 16 can determine the coordinates of any point in the frame of reference. It is understood that any type of coordinate system, including a spherical coordinate system, could be used and that the invention is not limited to the use of an x, y, z co-ordinate system.

The origin 24 could be a fixed point in the operating room such as the base of the stand 26 as shown in FIG. 1. For added stability, the stand 26 is secured to the room, for example, by bolting the stand 26 and the table upon which the patient 22 is situated to the room. Therefore the frame of reference comprises the fixed point 24', which is also the origin 24, and the frame of reference contains the ultrasound imaging transducer 18, the instrument 14, the origin 24 and at least the portion of the body 20 of the patient 22 which is of interest in the procedure being conducted. Points outside of the range of the spatial determinators 12, 16 need not be considered within the frame of reference. Therefore, the range of the first and second spatial determinators 12, 16 need not include the entire space of the room. The frame of reference with the fixed point 24' in the operating room being the origin 24 can be considered the laboratory or operating room frame of reference because the frame of reference is fixed with respect to the laboratory or operating room.

The first and second spatial determinators 12, 16 obtain or determine the spatial positional information of the instrument 14 and transducer 18, respectively, with respect to the origin 24 of the frame of reference. It is understood that the spatial positional information of the instrument 14 and ultrasound imaging transducer 18 need not be obtained with respect to the same point, namely the origin 24, but rather the position and orientation of the instrument 14 and transducer 18 could be obtained with respect to different points in the frame of reference provided the relative position of these different points is known. However, for convenience, it is preferable that the spatial positional information of the instrument 14 and the transducer 18 be obtained with respect to the same point, namely the origin 24.

In a further embodiment, the first spatial determinator 12 and the second spatial determinator 16 are arranged so that the relative position and orientation between the transducer 18 and instrument 14 is determined. This is accomplished, for example, by placing an electromagnetic emitter on one of the transducer 18 or instrument 14 and the sensor on the other of the instrument 14 and transducer 18.

Taking the case where the emitter is placed on the instrument 14, the origin becomes a movable or non-fixed origin in the operating room, shown generally in FIG. 1 by reference numeral 24". In this case, the frame of reference can be considered to be the instrument 14 frame of reference because the frame of reference is fixed with respect to the handle of the instrument 14. The movable origin 24" is movable with respect to the laboratory or operating room frame of reference, but the movable origin 24" is fixed in the frame of reference of the instrument 14.

The position and orientation of the instrument 14 in the instrument 14 frame of reference can be determined by knowing the dimensions of the instrument 14. Therefore, only one calculation would need to be made to determine the position and orientation of the transducer 18 in the instrument 14 frame of reference, namely calculating the relative position and orientation of the transducer 18 and images 32, with respect to the movable origin 24". This simplifies the calculations of this embodiment over the embodiment described above where the frame of reference is the laboratory frame of reference and the fixed point 24' is used as the origin 24 of the frame of reference. Also, only one emitter and one sensor are required when the frame of reference is with respect to the instrument 14. However, the emitter in the embodiment with the movable origin 24" must be located on the instrument 14. It is apparent that, in a similar manner, a movable origin could be associated with the transducer 18 so that a transducer 18 frame of reference is used.

As stated above, the spatial positional information of the instrument 14 and transducer 18 comprise the position and orientation of the instrument 14 and transducer 18, respectively, in a frame of reference, whichever frame of reference is used. Of course, the spatial positional information can comprise other information regarding the position of the instrument 14 or transducer 18 in the frame of reference, such as velocity, acceleration, or other information regarding the spatial position and orientation of the instrument 14 and the transducer 18 and the rate of change of the spatial position of the instrument 14 and transducer 18.

The ultrasound imaging transducer 18 emits ultrasonic waves into the body 20. The transducer 18 uses the echoes of these ultrasonic waves to produce image signals $S_I$ representing internal images of the body 20. The image signals $S_I$ are stored in an image processing unit 28.

In one preferred embodiment, the images 32 obtained by the transducer 18 comprise slice stacks of two dimensional images 32. Each of the two dimensional images 32 in each slice stack is obtained in a known position and orientation with respect to a fixed point 40 on the transducer 18. In this way, the slice stack of two dimensional images 32 form discrete images 32 taken within a volume or space shown generally in FIG. 2A by the dashed box 33. This volume or space 33 and the images 32 comprising the slice stack are uniquely defined with respect to the fixed point 40 by the vector position 42. In other words, the vector position 42 uniquely identifies the distance and direction of the volume 33 being imaged with respect to the fixed point 40 on the transducer 18 thereby uniquely identifying the position and orientation of each image 32 in the volume 33. The position and orientation of the images 32 in the volume 33 taken by the transducer 18 can be selected by the user and are generally fan shaped.

The system 10 further comprises a mapping unit 34. The mapping unit 34 receives the first spatial signal $Sp_1$ and the second spatial signal $Sp_2$. Using the first spatial signal $Sp_1$ and the second spatial signal $Sp_2$, the mapping unit 34 generates a first mapping signal $Sm_1$. The first mapping signal $Sm_1$ is indicative of the position and the orientation of the instrument 14 mapped onto the position of the images 32.

With the first mapping signal $Sm_1$, the image processing unit 28 can process the stored image signals $S_I$, and generate processed image signals $I_s$ from a view related to the spatial position of the instrument 14. The image processing unit 28 does this by re-sampling the stored image signals $S_I$, to generate processed image signals $I_s$ from a known position and orientation in the frame of reference. This known position is spatially related to the position and orientation of the instrument. In other words, the known position corresponds to a position on or near the instrument 14.

The processed image signals $I_s$ can be two-dimensional images along planes transaxial or orthogonal to the position of the instrument 14. The processed image signals $I_s$ can also be three-dimensional projection images. In either case, the processed image signals $I_s$ represent images of the body 20 from the view of the instrument 14, as if the observer was located at a position on or near the instrument 14 in the body 20 from which the image signals $S_I$, are re-sampled. In the case of three dimensional projection images, the processed images will have a view and a perspective which is spatially related to the position and orientation of the instrument 14.

Clearly, a view from the perspective of the instrument 14 is preferred over a view from the perspective of the transducer 18 because the perspective of the instrument 14 assists the medical practitioner to visualize the internal features of the body 20 while guiding the instrument 14. In addition, at the medical practitioner's discretion, the image processing unit 28 could generate processed images $I_s$ from another perspective, such as the perspective of the transducer 18, or, simply display the unprocessed signal images $S_I$, as is done in the prior art systems. Therefore, the present invention provides the medical practitioner with added versatility.

The display unit 30 receives the processed image signal $I_s$ and displays processed images 62 corresponding to the processed image signals $I_s$. The processed images 62 are the images acquired by the ultrasound imaging transducer 18 but generated from the view of the instrument 14 in the body 20 by the method described above. FIG. 1 shows an example of the processed images 62 from a view at a position just behind the end of the instrument 14, which in this case is a probe.

Because the spatial positional information for both the instrument 14 and the images 32 are obtained within the same frame of reference, the mapping unit 34 has sufficient information to map the position and orientation of the instrument 14 onto the position and orientation of the transducer 18. However, in order to map the spatial positional information of the instrument 14 onto the spatial positional information of the images 32, it is necessary that the mapping unit 34 determine the position and orientation of the images 32 in the frame of reference from the spatial positional information of the transducer 18. To accomplish this, the mapping unit 34 comprises a memory unit 38, which can be formed from standard memory chips, such as RAM or magnetic disc or other data storage devices, to store spatial positional information of the images 32 with respect to the transducer 18.

Figure 2A:
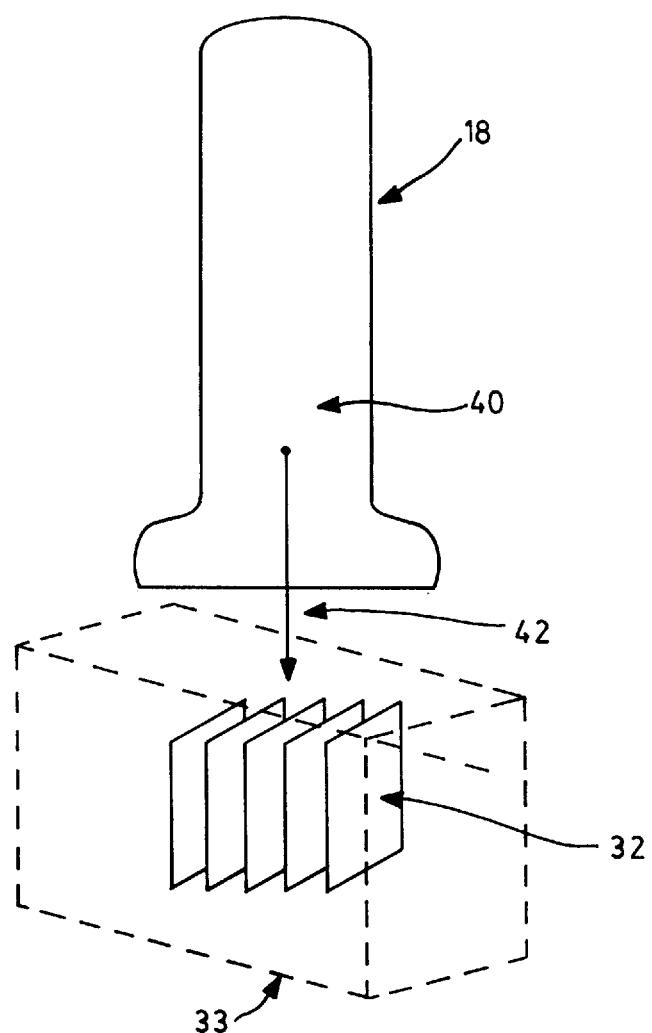
FIG. 2A shows an enlarged view of an ultrasound imaging transducer used in one embodiment of the present invention.

The spatial positional information of the images 32 with respect to the transducer 18 comprises the vector position 42. The vector position 42 from the fixed point 40 essentially represents the distance and direction from which the transducer 18 is acquiring the images 32 within the body 20 as shown in FIG. 2A.

The vector position 42 can be determined by calibrating the transducer 18 prior to commencement of the procedure. In general, the vector position 42 will not vary greatly during the procedure and recalibration of the transducer 18 is not generally required. Moreover, depending on the type of transducer 18 used, the calibration may not be required to be performed at all but may be set during manufacture and be sufficiently stable that it does not vary.

In some embodiments, the transducer 18 may be capable of adjustments so that the depth, or other position, of the images 32 with respect to the transducer 18 can be adjusted. In these cases, it is apparent that a different vector position 42 from the fixed point 40 would be required for each change in the depth of the images 32 with respect to the body 20. The spatial positional information of the images 32 with respect to the transducer 18 stored in the memory unit 38 would comprise the vector position 42 for images 32 having varying depths within the body 20. An adjustment of the depth of the images 32 within the body 20 would cause the mapping unit 34 to select a corresponding vector position 42 from the memory unit 38.

With the spatial positional information of the images 32 with respect to the transducer 18 and the second spatial signal $Sp_2$, which represents the spatial positional information of the transducer 18 in the frame of reference, the mapping unit 34 can determine the position of the images 32 in the frame of reference. The mapping unit 34 accomplishes this by adding the vector position 42 of the images 32 with respect to the fixed point 40 on the transducer 18, which information is stored in the memory unit 38, to the spatial positional information of the transducer 18 represented by the second spatial signal $Sp_2$.

It is preferred that the second spatial signal $Sp_2$ represent the spatial positional information of the fixed point 40 of transducer 18. However, if this is not the case, and the second spatial signal $Sp_2$ represents the spatial positional information of another fixed point (not shown) on the transducer 18, then the mapping unit 34 can perform a further addition from the other fixed point (not shown) to the fixed point 40.

The mapping unit 34 comprises a processing unit 39 for performing these additions. The processing unit 39 also maps the spatial positional information of the instrument 14, represented by the first spatial signal $Sp_1$, onto the spatial positional information of the images 32.

Figure 2B:
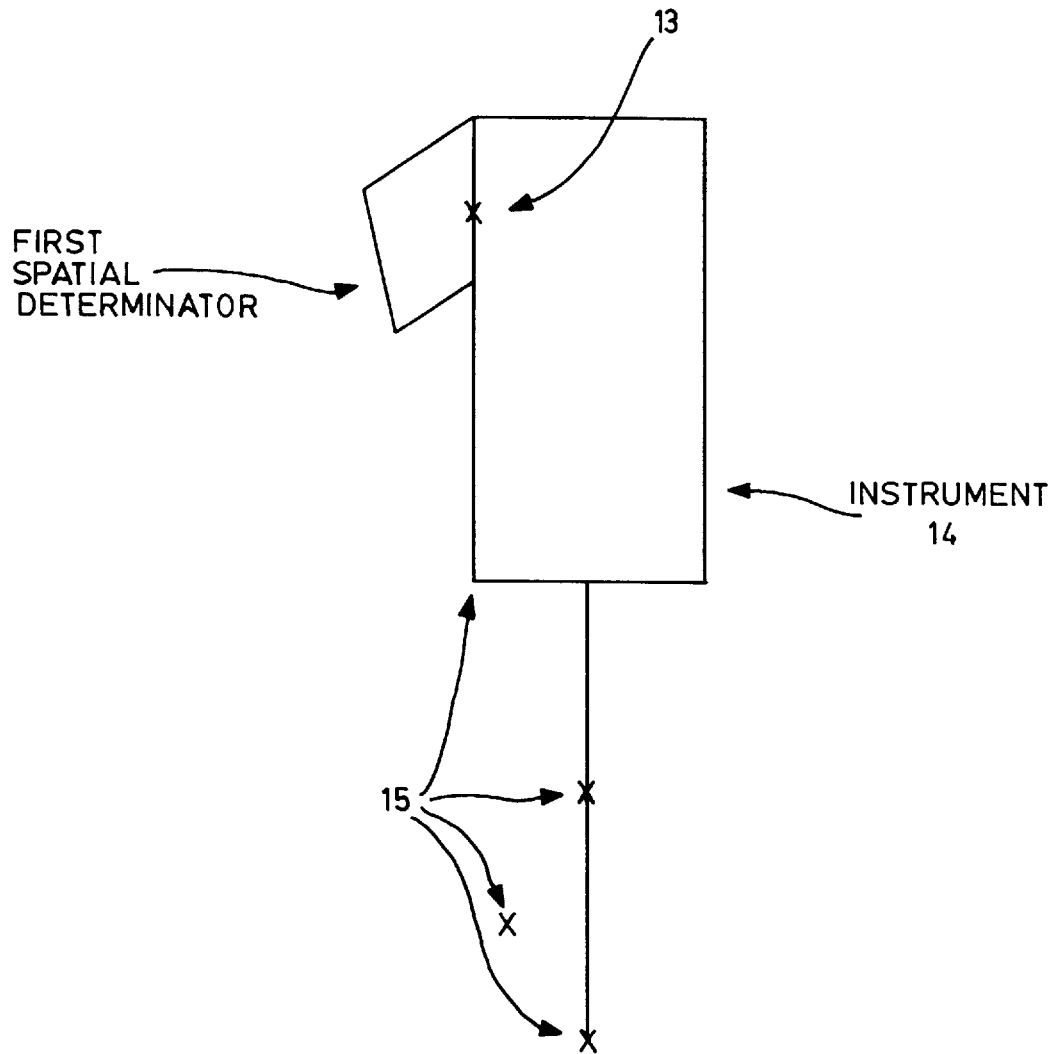
FIG. 2B shows an enlarged view of one instrument which may be used in an embodiment of the present invention.

In a preferred embodiment, spatial positional information for parts 15 (identified by "x" on FIG. 2B) of the instrument 14 are determined. The parts 15 of the instrument 14 could be any easily-observable location on or near the instrument 14, such as the end of a syringe or probe, or, a point a known distance back from the end of a syringe or probe. The parts 15 could also include points a known distance from the instrument 14. In any case, the spatial positional information of the parts 15 of the instrument 14 are determined with respect to a point 13 fixed to the instrument 14 by measuring or calibrating the instrument 14. Alternatively, so called "smart" instruments, which generate signals indicative of their shape, could be used so that the position of the parts 15 of the "smart" instrument with respect to a point 13 fixed to the instrument 14 could be easily assessed.

Once the position of the parts 15 of the instrument 14 with respect to a point 13 fixed to the instrument is determined, this information is stored in the memory unit 38. The spatial positional information of the parts 15 of the instrument 14 can be determined with respect to the frame of reference by the processing unit 39 combining the spatial positional information of the point 13 fixed to the instrument 14 with the spatial positional information of the parts 15 of the instrument 14 with respect to the point 13 fixed to the instrument 14. Preferably, the point 13 fixed to the instrument 14 corresponds to the location where the first spatial determinator 12 is attached to the instrument 14. Otherwise, the processing unit 39 can perform an additional step of deriving the spatial positional information of the point 13 fixed to instrument 14 from the first spatial signal $Sp_1$. With this information, the mapping unit 34 maps the parts 15 of the instrument 14 onto the position of the images 32. The mapping signal $Sm_1$ will then be indicative, not only of the position of the instrument 14, but also the position of the parts 15 of the instrument 14 with respect to the position of the images 32. This permits the image processing unit 28 to generate processed image signals $I_s$ from a view which is related to the spatial position of one of the parts 15 of the instrument 14. The precise view to be displayed on the display unit 30 can be selected by the user of the system 10.

The ultrasound imaging transducer 18, in a preferred embodiment, continuously acquires images 32 of the body 20. More preferably, the images 32 are acquired quickly with a small time lag between successive images. Still more preferably, the ultrasound transducer 18 acquires the images 32 in real time or substantially real time, such that no time lag or a negligibly small time lag, such as less than one second, will occur between subsequent sampling of the images 32.

In this way, the images 32 can be displayed in a sequence in order to show movement of the body 20 and the internal features of the body 20 in substantially real time. Likewise, the spatial positional information of the instrument 14 can be periodically sampled and mapped onto the images 32 of the body 20. Thus, the processed images 62 displayed on the display unit 30 will change over time corresponding to changes of the position and orientation of the instrument 14 relative to the body 20. The processed images 62 being displayed will generally be based on the most recent images 32 and information. This allows the user of the system 10 to track changes in the body 20 of the patient 22 as well as movement of the instrument 14 within the body 20. In this way, the user has the ability to follow movement of the instrument 14 and to see how the instrument 14 affects the internal functions of the body 20 during a medical procedure.

In a preferred embodiment, as shown in FIG. 1, the body 20 is the anatomical body 20 of the patient 22. In this embodiment, the instrument 14 can be a surgical instrument and may be a syringe, a probe or other type of surgical instrument.

The slice stack of two dimensional images 32 can be pre-processed prior to display in order to enhance certain anatomical features of the anatomical body 20 as is known in the art. This enhancement can take the form of colouring certain tissues representing particular organs with different colours so that the generated enhanced internal images clearly distinguish different anatomical features in the anatomical body 20. Such pre-processing of the slice stack of two dimensional images 32 can be performed by the image processing unit 28 in a known manner.

Likewise, as is also known in the art, the slice stack of two dimensional images 32 can be combined to form a three dimensional representation of the anatomical features in the anatomical body 20. In this way, the image processing unit 28 can generate processed images $I_s$ comprising a three dimensional projection of the volume or space 33 within the body 20, and, from the perspective of the instrument 14 within the body 20.

If the ultrasound imaging transducer 18 is a three dimensional imaging transducer, then the image signals $S_I$ will comprise a three dimensional representation of the body 20. Likewise, the images stored in the image processing unit 28 and the processed images 62 displayed on the display unit 30 will be three dimensional images.

As stated above, the first mapping signal $Sm_1$ is indicative of the position of the instrument 14 mapped onto the position of the images 32. The first mapping signal $Sm_1$ can also consist of video information sufficient to display a representation of the instrument 14 on the display unit 30 in a position with respect to the images 32 corresponding to the position of the instrument 14 with respect to the body 20. Alternatively, the first mapping signal $Sm_1$ can comprise sufficient information regarding the position, and if desired orientation, of the instrument 14 so that another unit, such as the image processing unit 28, can generate a representation 36 of the instrument 14. A representation 36 of the instrument 14 will be displayed if, for example, the user selects a view or perspective such that a part of the instrument 14 is visible. FIG. 1 shows the embodiment where the image processing unit 28 receives the first mapping signal $Sm_1$ and generates a representation 36 of the instrument 14. The representation 36 of the instrument 14 can be incorporated in the processed image signals $I_s$.

In one embodiment, the images 32 can be pre-processed by the image processing unit 28 to provide a three dimensional representation of the anatomical features within the body 20. In this embodiment, a representation 36 of the instrument 14, also three dimensional, could be displayed on the display unit 30 if the instrument is visible in the perspective and view selected. This gives the user of the system 10 the appearance and feel of a surgical procedure but without the necessity for a large incision into the body 20 of the patient 22.

It is apparent that one advantage of the present system 10 and method of using the system 10 is that the step of determining the position, and if desired orientation, of the instrument 14 relative to the position, and if desired orientation, of the images 32 is independent of the position of the body 20 in the frame of reference. In other words, all of the values used by the mapping unit 34 to map the spatial positional information of the instrument 14 onto the spatial positional information of the images 32 is independent of the position or orientation of the body 20. This means that the patient 22 need not be kept stable during the procedure. The patient 22 can move around during the procedure for increased comfort. Also, the patient 22 can be moved during the procedure to view aspects of the patient's anatomy from different locations or in motion.

Figure 3A:
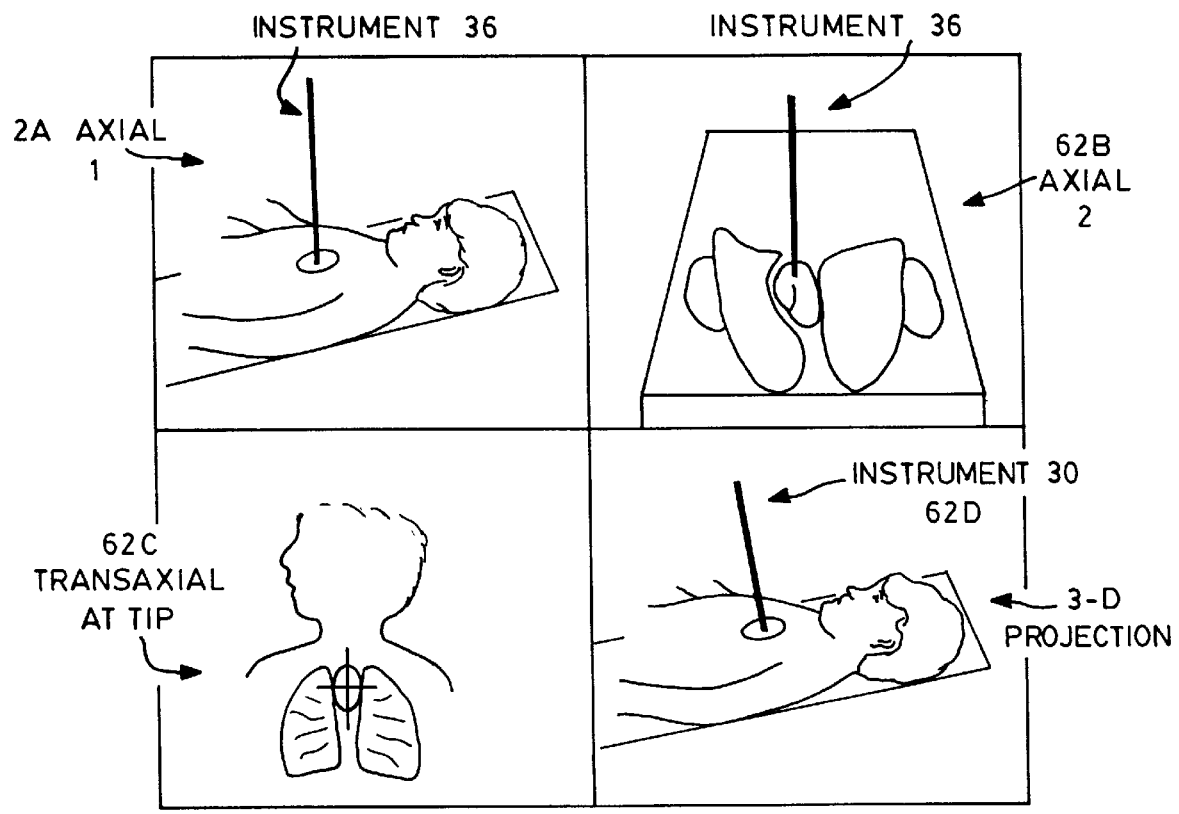
FIGS. 3A and 3B show processed images which can be generated by the system according to one embodiment of the present invention.
Figure 3B:
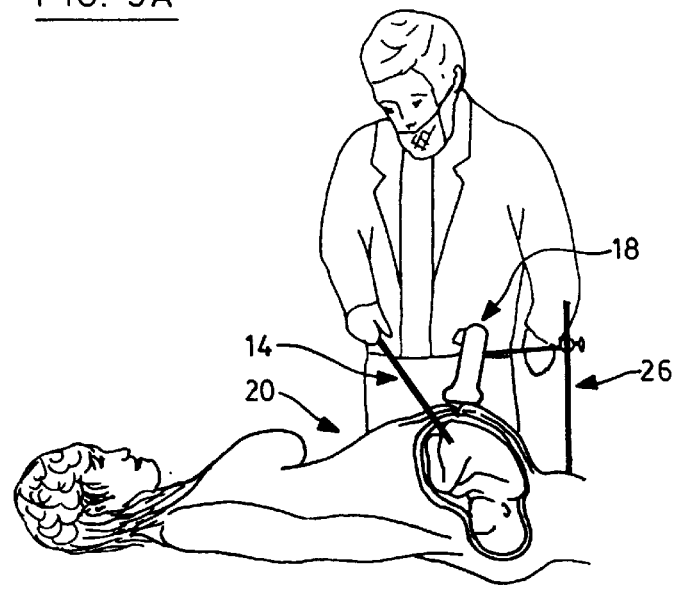

FIGS. 3A and 3B show the possible views which can be displayed using the method and system 10 of the present invention. As shown in FIGS. 3A and 3B, a fetal cardiac procedure is being performed on a patient 12. The instrument 14 is being inserted into the fetus of patient 22. The position and orientation of the instrument 14 and transducer 18 are being determined by using the system 10 and method described above. FIG. 3B shows the possible views which can be generated by the system 10.

All of the processed images 62A, 62B, 62C and 62D shown in FIG. 3A have been generated from a view spatially related to the spatial position of the instrument 14. For example, processed image 62A is an axial 1 view taken from a spatial position along a first axis of the instrument 14. Processed image 62A shows the fetus and a representation 36 of the instrument 14. Likewise, processed image 62B is an axial 2 view taken from a spatial position along a second axis of the instrument 14, and, shows the fetus and a representation 36 of the instrument 14. Processed image 62C is an image of a slice through the fetus transaxial to the instrument 14. The slice plane is perpendicular to the axis of the instrument 14, and the tip of the instrument 14 is located at the centre of the slices and marked on the image with a cursor "+".

The slice planes "axial 1", "axial 2" and "transaxial at tip" are all associated with the position and orientation of the instrument 14, such that moving the instrument 14 causes a change to the corresponding images 62A, 62B and 62C.

Processed image 62D is a three dimensional projection of the fetus generated from the images 32 acquired by the transducer 18. A three dimensional representation 36 of the instrument 14 also appears in processed image 62D. The view of processed image 62D is generated from a position a predetermined distance from the side of the instrument 14, and from a perspective looking towards the instrument 14 so that the representation 36 of the instrument 14 can be seen in the processed image 62D.

It is apparent that each of the views of the processed images 62A, 62B, 62C and 62D are taken or generated from a spatial position, whether a point or an axis, which is spatially related to the position of the instrument 14 in that it is along an axis or from a point on or near the instrument 14. This is the case even though the processed images 62A, 62B, 62C and 62D are generated from the image 32 acquired by the transducer 18.

Figure 4:
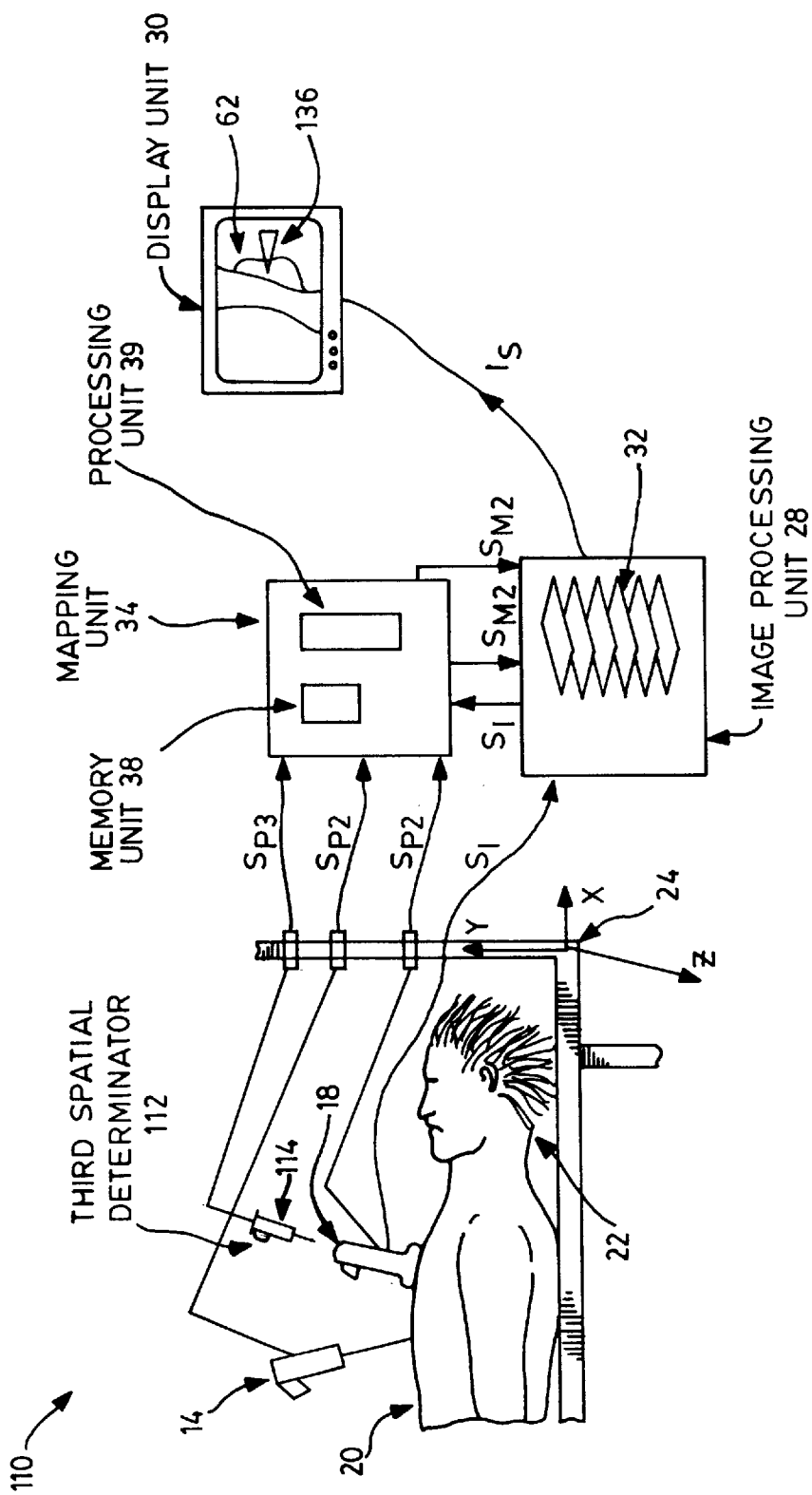
FIG. 4 shows a system according to another embodiment of the present invention where two instruments are used.

FIG. 4 shows a further preferred embodiment of the present invention. The system 110 shown in FIG. 4 has several common elements to system 10 shown in FIG. 1, and like reference numerals are used for like features. However, the system 110 is an expansion of the system 10 in that another instrument 114 is used in addition to the instrument 14. The system 110 comprises a third spatial determinator 112 for determining spatial positional information of the other instrument 114 in the frame of reference. The third spatial determinator 112 sends a third spatial signal $Sp_3$ to the mapping unit 38 in the same manner as the first spatial determinator 12 sends the first spatial signal $Sp_1$ to the mapping unit 34. The third spatial signal $Sp_3$ represents the spatial positional information of the other instrument 114 in the frame of reference.

The mapping unit 34 receives the third spatial signal $Sp_3$ and generates a second mapping signal $Sm_2$ indicative of the position of the other instrument 114 mapped onto the position of the images 32. The image processing unit 28 receives the second mapping signal $Sm_2$ and generates a representation 136 of the other instrument 114 having a position, and if desired orientation, relative to the images 32 of the body 20 which corresponds to the position, and if desired orientation, of the other instrument 114 relative to the body 20. The representation 136 of the other instrument 114 will appear on the display unit 30 when the other instrument 136 can be seen in the processed images 62.

Also, the user could select a view from a view spatially related to the other instrument 114. In this case, the image processing unit 28 can generate the processed image signals $I_s$ from the view of the other instrument 114. A representation 36 of the instrument 14 would then be generated and appear on the display unit 30.

It is understood that the system 110 can be further expanded so that three or more medical instruments or probes can be tracked and a representation of them displayed on the display unit 30 in the same manner as representations of the instrument 14 and the other instrument 114 are displayed.

Figure 5:
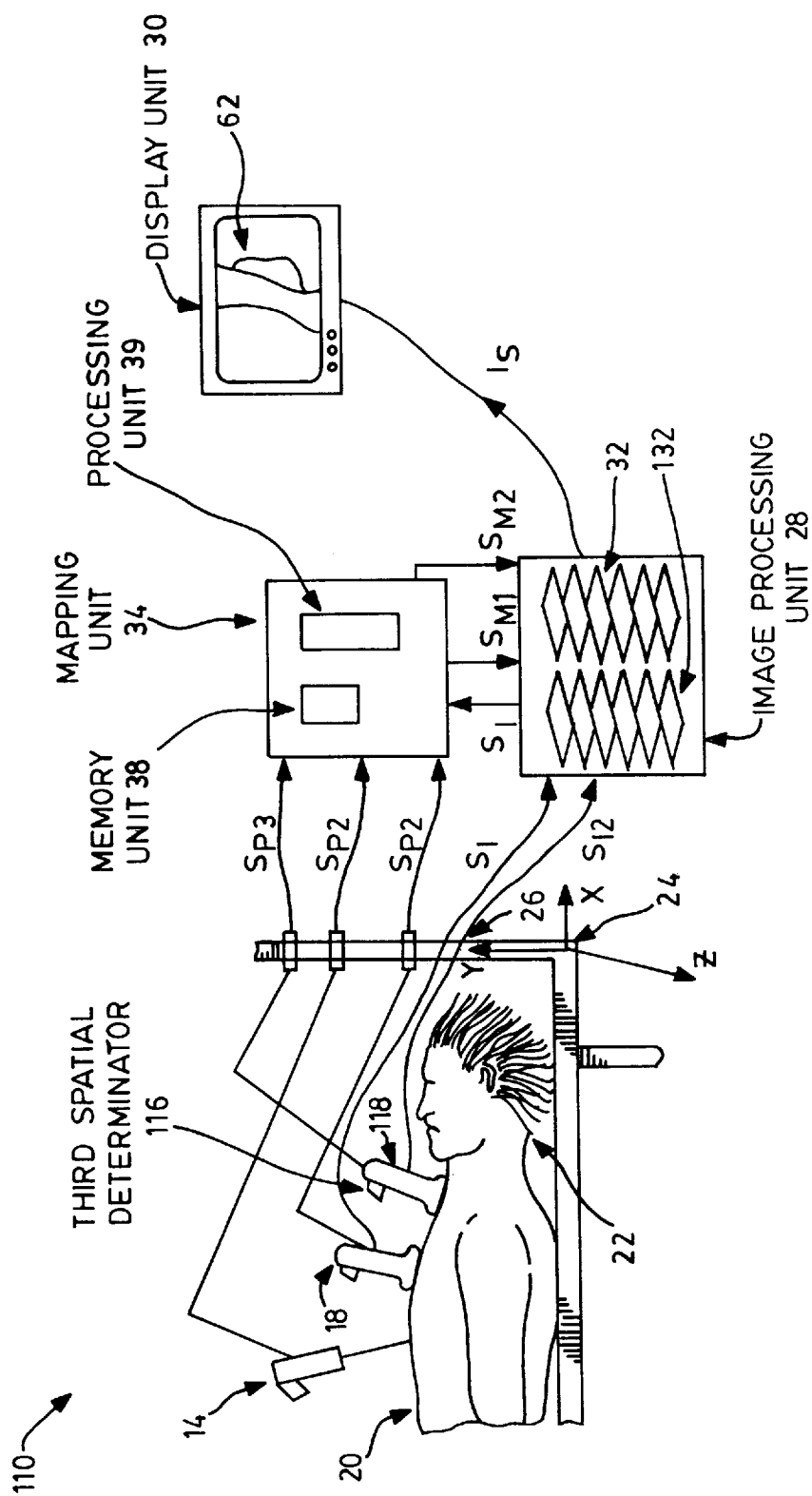
FIG. 5 shows a system according to another embodiment of the present invention where two ultrasound imaging traducers are used.

In addition, the systems 10 and 110 can be expanded so that more than one transducer 18 is used. FIG. 5 shows a further embodiment, similar to the embodiment shown in FIG. 4, but with an additional transducer 118 acquiring images to be stored in the image processing unit 28 and used to generate the processed image signal $I_s$ in the same manner as discussed above with one transducer 18.

The additional transducer 118 sends a second image signal $SI_2$ to the image processing unit 28 representing the images acquired. The image processing unit 28 stores the images acquired by the additional transducer 118 in a second slice stack 132. The second slice stack 132 and the slice stack 32 are used by the processing unit 28 to generate the processed image signals $I_s$. The position and orientation of the additional transducer 118 is determined by the third spatial determinator 116 in the same manner as described above for the other instrument 114. Likewise, the position and orientation of the images 32 acquired by the additional transducer 118 can be determined in the same manner as described above with respect to the transducer 18.

The principle advantage of the additional transducer 118 is to acquire additional images 132 which could not be acquired by the transducer 18, either because the transducer 18 cannot scan a large enough volume, or because part of the ultrasound signals emitted from the transducer 18 are blocked, for example, by bone or cartilage. In either case, by utilizing the two slice stacks 32, 132, the image processing unit 28 can generate processed image signals $I_s$ depicting views of the body 20 which could not be generated if only one transducer 18 or 118 were used. This principle can be extended to more than two transducers 18, 118 if desired.

While reference has been made to an anatomical body 20 of a patient 22, it is understood that the present method and systems 10, 110 can be used in association with any body 20 which can be imaged by an ultrasound imaging transducer 18. Likewise, while the present invention has been described in terms of a surgical instrument 14, it is understood that the invention is not restricted to a surgical instrument 14. Rather, the present method and systems 10, 110 can be used in association with any type of instrument or device.

It will be understood that, although various features of the invention have been described with respect to one or another of the embodiments of the invention, the various features in the embodiments of the invention may be combined or used in conjunction with other features or embodiments of the invention as described and illustrated herein.

Although this disclosure has described and illustrated certain preferred embodiments of the invention, it is to be understood that the invention is not restricted to these particular embodiments. Rather, the invention includes all embodiments which are functional, mechanical or electrical equivalents of the specific embodiments and features that have been described and illustrated herein.

The embodiments of the invention in which an exclusive property or privilege is claimed are defined as follows:

1. A system for visualizing internal images of a body in relation to an instrument within the body, said images having been acquired by an ultrasound imaging transducer, the system comprising:

first spatial determinator means for determining spatial positional information of the instrument comprising a position and an orientation of the instrument in a frame of reference and for sending a first spatial signal representing the spatial positional information of the instrument;

second spatial determinator means for determining spatial positional information of the ultrasound imaging transducer comprising a position and an orientation of the ultrasound imaging transducer in the frame of reference and for sending a second spatial signal representing the spatial positional information of the transducer;

mapping means for receiving the first spatial signal and the second spatial signal and generating a first mapping signal indicative of the position and orientation of the instrument relative to the position and orientation of the images;

image processing means for receiving the first mapping signal and signals representing the images acquired by the transducer and generating processed images from a view which is spatially related to the position of the instrument; and display means for displaying the processed images.

2. The system as claimed in claim 1 wherein the image processing means generates a representation of the instrument based on the first mapping signal, said representation of the instrument having a position relative to the processed images of the body corresponding to the position of the instrument relative to the body.

3. The system as claimed in claim 1 wherein the mapping means comprises:

memory means for storing spatial positional information of the images with respect to the transducer; and processing means for determining the position of the images in the frame of reference from the second spatial signal and the spatial positional information of the images with respect to the transducer stored in the memory means and for mapping the position of the instrument onto the position of the images to generate the first mapping signal.

4. The system as claimed in claim 3 wherein the spatial positional information of the images with respect to the transducer stored in the memory means comprises a vector position of the images acquired by the transducer with respect to a fixed point on the transducer determined by calibrating the transducer;

wherein the second spatial signal representing the spatial positional information of the transducer comprises a position of the fixed point on the transducer in the frame of reference; and wherein the processing means determines the spatial position of the images in the frame of reference by adding the vector position of the images with respect to the fixed point on the transducer to the spatial positional information of the fixed point on the transducer.

5. The system as claimed in claim 4 wherein the images of the body comprise a sequence of three dimensional images which can be displayed in a sequence in substantially real time; and wherein the view of the processed images displayed on the display change corresponding to changes in the position and orientation of the instrument relative to the body; and wherein the image processing means generates a three dimensional representation of the instrument on the display, said representation having a position and an orientation relative to the processed images corresponding to the position and orientation of the instrument relative to the body.

6. The system as claimed in claim 5 wherein the three dimensional images have a view and a perspective which is spatially related to the position and orientation of the instrument.

7. The system as claimed in claim 4 wherein the body is an anatomical body and the instrument is a surgical instrument.

8. The system as claimed in claim 4 further comprising:

third spatial determinator means for determining spatial positional information of an other instrument comprising a position and an orientation of the other instrument in the frame of reference and for sending a third spatial signal representing the spatial positional information of the other instrument;

wherein the mapping means receives the third positional signal and generates a second mapping signal indicative of the position and orientation of the other instrument mapped onto the position and orientation of the images; and wherein the image processing means receives the second mapping signal and generates processed images from a view related to the spatial position of the instrument or the other instrument dependent upon a user selection.

9. The system as claimed in claim 4 further comprising:

third spatial determinator means for determining spatial positional information of an additional ultrasound imaging transducer acquiring images of the body comprising a position and an orientation of the additional transducer in the frame of reference and for sending a third spatial signal representing the spatial positional information of the additional transducer;

wherein the mapping means receives the third positional signal and generates a second mapping signal indicative of the position and the orientation of the instrument relative to a position and an orientation of the images acquired by the additional transducer;

wherein the image processing means receives the second mapping signal and signals representing the images acquired by the additional transducer and generates processed images from a view related to the position and the orientation of the instrument, based on the signals representing the images acquired by the transducer and the additional transducer.

10. The system as claimed in claim 4 wherein the instrument has parts and the memory means stores spatial positional information of the parts of the instrument with respect to a point fixed to the instrument;

wherein the first spatial signal represents spatial positional information of the point fixed to the instrument;

wherein the processing means determines spatial positional information of the parts of the instrument in the frame of reference based on the first spatial signal and the spatial positional information of the parts of the instrument with respect to the point fixed to the instrument;

wherein the processing means maps the position of the parts of the instrument onto the position of the images such that the first mapping signal is indicative of the position of one of the parts of the instrument relative to the position of the images; and wherein the image processing means generates processed images from a view spatially related to the position of one of the parts of the instrument in the body.

11. The system as claimed in claim 3 wherein the image processing means stores the acquired images with the spatial positional information of each image in a slice stack of two dimensional images.

* * * * *